United States Patent [19]

Albert et al.

[11] Patent Number: 4,486,534
[45] Date of Patent: Dec. 4, 1984

[54] PROCESS FOR THE PREPARATION OF IMMUNOLOGICALLY ACTIVE ENZYME TAGGED CONJUGATES

[75] Inventors: Winfried Albert, Pähl; Helmut Lenz, Tutzing, both of Fed. Rep. of Germany

[73] Assignee: Boehringer Mannheim GmbH, Mannheim, Fed. Rep. of Germany

[21] Appl. No.: 379,794

[22] Filed: May 19, 1982

Related U.S. Application Data

[63] Continuation of Ser. No. 145,902, May 2, 1980, abandoned.

[30] Foreign Application Priority Data

Jun. 7, 1979 [DE] Fed. Rep. of Germany ....... 2923139

[51] Int. Cl.$^3$ .......................... G01N 33/54; C12N 9/96
[52] U.S. Cl. .......................................... 435/188; 435/7; 435/177; 435/178; 436/543; 436/544; 436/547
[58] Field of Search ....................... 435/4, 7, 174, 177, 435/188, 805, 810, 178; 436/543, 544, 547

[56] References Cited

U.S. PATENT DOCUMENTS 3,852,157 12/1974 Rubenstein et al. .................... 435/7
4,150,033 4/1979 Kitagawa ................................ 435/7

OTHER PUBLICATIONS

Kurger et al., *An Introduction to Separation Science*, John Wiley & Sons, N.Y. (1973), pp. 402–406.
Aurameas et al., "Coupling of Enzymes to Antibodies and Antigens", *Scand. J. Immunol.* vol. 8, Suppl. 7 (1978), pp. 7-23.

*Primary Examiner*—Esther M. Kepplinger
*Attorney, Agent, or Firm*—Felfe & Lynch

[57] ABSTRACT

A process for the preparation of immunologically active tagged conjugates by covalent linking of an enzyme with an antigen or haptene, which process comprises placing a solution of a mixture of immunologically active and inactive conjugates in contact with an insoluble complex former able to form a non-immunological complex reversibly with the untagged antigen or haptene component of the conjugate, separating the insoluble complex former, and eluting with a desorbent for untagged antigen or haptene.

10 Claims, No Drawings

PROCESS FOR THE PREPARATION OF IMMUNOLOGICALLY ACTIVE ENZYME TAGGED CONJUGATES

This is a continuation application of Ser. No. 145,902 filed May 2, 1980.

The present invention relates to a process for the preparation of immunologically active, enzyme-tagged conjugates, which, in immunological identification methods, adapt themselves to competing with the corresponding untagged antigen or haptene for the linkage to the antibody.

Recently, the enzyme-immuno-assay (EIA) has increasingly been introduced alongside the radio-immuno-assay (RIA), which has been known for a longer time, but its radioactive tagging is replaced by enzyme tagging. In the enzyme-immuno-assay, a known quantity of enzyme-tagged antigen or haptene competes with the unknown quantity of the untagged antigen or haptene that is being sought and that is present in the sample under investigation for the linkage to a common antibody. The quantity of enzyme-tagged antigen or haptene bound to the antibody, usually designated as conjugate, is a measure of the quantity of antigen or haptene sought.

For this enzyme-immuno-assay, conjugates are needed that are immunologically active. In the preparation of conjugates by tagging the antigen or haptene, however, a considerable, usually predominant fraction of immunologically inactive conjugates is formed. Such mixtures of immunologically active and inactive conjugates, however, are usually little suited for the enzyme-immuno-assay, since they do not permit the achievement of the sensitivity and accuracy, possible in themselves, of the test system. In the conjugate, for example, the immunological properties of the immune reagent with enzymes may be changed, and thus, a loss of antigen determinants or linkage positions or a reduced affinity for the linking partner may result (cf. Clin. Chem. Acta 81, 1 to 40 (1977)).

Processes are known, based on gel chromatography or immune adsorption, for the purification of the raw conjugate mixtures, which usually shown only a small percentage of products with the properties sought, such as high immune reactivity and high enzyme activity. In conjugate purification through immune adsorption, excessively large losses of activity appear, since there are no elution agents that split the immune complexes without inactivating the tagging system or changing the antigenic properties. In gel chromatography, unsatisfactory separation results are obtained, since the properties of the active and the inactive conjugates that are decisive for this can hardly be distinguished.

The present invention is, therefore, based on the task of eliminating the disadvantages portrayed above, and creating a process which, in a simple way, will make possible a satisfactory separation (purification) of the raw conjugate mixtures from immunologically active and inactive conjugates.

According to the present invention, this problem is solved by means of a process for the preparation of immunologically active enzyme-tagged conjugates by covalent linkage of an enzyme to an antigen or haptene, with the formation of a mixture of immunologically active and inactive conjugates, characterized by putting a solution of this mixture into contact with an insoluble complex former, which is able to form, reversibly, a non-immunological complex with the untagged antigen or haptene component of the conjugate, separating the insoluble complex-formers, and eluting with a desorbent for untagged antigen or haptene.

Surprisingly, it has been shown, and the present invention is based on this, that the adhesiveness or adsorption to such adsorbents is dependent on the immunological activity, in such a way that the immunologically active conjugates are more strongly adsorbed than the immunologically non-active ones, so that even the immunologically inactive or less active conjugates are more easily eluted than the immunologically active conjugates.

Within the framework of the present invention, those insoluble complex-formers which are rendered insoluble by linkage to an insoluble carrier material and/or cross-linking are preferred.

Suitable complex-formers for the particular antigens or haptenes are generally known to the expert. If, for example, a protein without enzymatic properties is involved in the case of the antigen; e.g., steroid-linking protein, serum albumin, or TBG (thyroxin-binding globulin), then the corresponding linkage components, for example, a steroid, fatty acid, thyroxine or the like, in insolubilized form, will be used as the adsorbent. If an enzyme is involved in the case of the antigen, then a co-enzyme, a substrate, an analog of it, or an inhibitor of it may expediently be used as a complex-former. Conversely, in using a hormone, either a hormone-linking protein or a low-molecular complex-forming substance will be used. If the haptene is a carbohydrate, then lectine, for example, is suitable as a complex-former.

Methods for the insolubilization of such complex-formers to suitable carrier substances; such as, for example, cellulose, glass, agarose, and the like, are known to the expert, and need not be described here in any further detail. The same thing is true for the process for insolubilizing by cross-linking with polyfunctional cross-linking agents, for example, dialdehyde, as well as glutardialdehyde, diepoxides, and the like. For these cross-linking reactions for insolubilization, accordingly, the same thing is true as for insolubilization with a carrier material. Suitable insolubilization methods are described, for example, in Colowick-Kaplan, Methods in Enzymology, 44, 11–134, 263–291 (1976).

An analagous substance or the complex-former itself in dissolved form may expediently be used as an eluting agent. Detergents may also be considered. It is important that an eluting agent be selected that does not significantly affect the activity of the tagging enzyme. Complex formation and elution are always carried out in a buffered solution with a pH-value suitable for the tagging enzyme.

Typical examples of antigens and haptenes which, according to the present invention, can be purified in enzyme-tagged form are TBG, serum albumin, ligandin, steroid-binding protein, cyclo-GMP-binding protein, dehydrogenases, phospholipase, insulin, carbohydrates, thyroxine, triiodothyronine, digoxine, steroid hormones, and endorphine.

Typical examples of suitable complex-formers for the antigens and haptenes named above are thyroxine ($T_4$), triiodothyronine ($T_3$), fatty acid, ligandin-ligand, steroid, cyclo-AMP cyclo-GMP, NAD(H), lipoprotein, insulin receptor, and the specific binding proteins for the haptenes; such as lectin, TBG, serum albumin, bovine serum albumin, charge transfer-ligand, steroid-binding globulin, and morphine receptor. Even pure chemical complex-formers, such as phenylbutylamine for $T_4$ and $T_3$, may be used.

In the table below, suitable antigens and haptenes, with the appropriate complex-formers and eluting agents, are shown as examples within the framework of the present invention.

TABLE

| Enzyme-tagged Antigen or Haptene | Complex-formers, bound to carriers, (insoluble) | Elution agent (dissolved) |
|---|---|---|
| 1  TBG | $T_4$- ($T_3$-sepharose) | $T_4$ or ANS[1] or salicylate |
| 2  serum albumin | fatty acid | free fatty acid, detergent |
| 3  ligandin | ligandin-ligand | free ligandin, ligand |
| 4  steroid-binding protein | steroid | free steroid |
| 5  c-AMP-binding protein | c-AMP | dissolved c-AMP |
| 6  c-GMP-binding protein | c-GMP | dissolved c-GMP |
| 7  dehydrogenases | NAD(H) | NAD(H) in solution |
| 8  phospholipase | lipoprotein | desoxycholate |
| 9  insulin | insulin receptor | insulin |
| 10  carbohydrate | lectin | dissolved sugar |
| 11  $T_4$ ($T_3$) thyroxine (triiodothyronine) | TBG | $T_4$, $T_3$ or ANS[1] |
| 12  $T_4$ ($T_3$) thyroxine (triiodothyronine) | serum albumin | barbiturate, ANS[1] |
| 13  $T_4$ ($T_3$) thyroxine (triiodothyronine) | phenylbutylamine | non-ionic detergent |
| 14  digoxine | bovine serum albumin | barbiturate |
| 15  digoxine | charge transfer ligand | ligand in solution |
| 16  steroid hormone | steroid-binding globulin | steroid in solution, detergent |
| 17  endorphine | morphine receptor | morphine or analogs |

[1]ANS = anilinonaphthaline sulfonic acid

The process according to the present invention makes it possible, in a single simple concentrating step, to remove the greatest part of the immunologically inactive conjugate and obtain an immunologically active conjugate, which exhibits a superior suitability for immunological detection procedures.

The following examples explain the present invention further.

EXAMPLE 1

(a) Sepharose 4B is activated according to the usual method with cyanogen bromide, and charged with such a quantity of bovine serum albumin that about 5 to 15 mg of albumin is fixed per ml of sepharose.

(b) Glucose oxidase (EC. 1.1.3.4 from mold) is made to react with 5 to 10 times a molar excess of activated digoxine derivative (activation consists of a N-hydroxysuccinimide ester function, which is bound covalently to the glycoside part of the digoxine molecule), and, after a reaction period of about 24 to 48 hours at 4° C., is separated from the excess digoxine derivative by dialysis. The primary conjugate shows an immune reactivity of about 6%, i.e., 6% of the glucose oxidase in the dialyzed reaction mixture is bound to an immune adsorber, which bears an excess of antidigoxine-antibody.

(c) The primary conjugate is arranged in layers in a phosphate buffer (for example, 0.2M, pH 7) over a column filled with bovine serum albumin-sepharose. After washing out the non-binding GOD-activity with phosphate buffer, the interesting conjugate is eluted with 0.12M barbiturate buffer, pH 8 (range 7.5 to 9). The chromatography is given such dimensions that about 20 ml of albumin sepharose/5 mg GOD is put into the primary conjugate. The purified conjugate is up to 90% immune-reactive in the sense defined above.

EXAMPLE 2

(a) Thyroxine-binding globulin (TBG), a glycoprotein, is activated with periodate, after Nakane and Kawaoi (J. Histochemistry, Cytochemistry, 22,,1084–1091 (1974)), and in the pH-range of 8 to 10, made to enter a coupling reaction with 10 to 30 times the amount by weight of $\beta$-galactosidase (EC 3.2.1.23, from E. coli). After reduction with sodium borhydride and dialysis, a primary coupling product results, which, according to the exact selection of the pH-conditions, reaction periods, and proportions, is up to 5 to 20% immune-reactive (in the sense of % of binding of the $\beta$-galactosidase activity present in the coupling mixture to an immuneadsorbent with an antibody against TBG).

(b) Thyroxine is fixed in a stable, covalent linkage, according to Kagedal and Kaellberg (Clin. Chim. Acta 78, 103 (1977)), to epoxy sepharose 6B (Pharmacia). A column is packed with about 3 ml of thyroxine sepharose per 1 mg of TBG in the conjugate mixture, and equilibrated with 10 to 50 mM TRIS/0.1M NaCl/10 mM $MgCl_2$-buffer, pH 7.5 to 8.5. The raw conjugate mixture (dialyzed against the same buffer) is slowly placed onto this column and washed with buffer until no more $\beta$-galactosidase activity can be detected.

Then specifically bound conjugate is eluted with buffer, to which 2 to 10 mM anilinonaphthaline sulfonic acid (an agent that specifically displaces thyroxin from the linkage with TBG) has been added. The $\beta$-galactosidase activity in the eluate binds up to $\geq 80\%$ to the anti-TBG-immune-adsorbent.

It will be understood that the specification and examples are illustrative but not limitative of the present invention and that other embodiments within the spirit and scope of the invention will suggest themselves to those skilled in the art.

What is claimed is:

1. In a process for the preparation of immunologically active enzyme-tagged conjugates, the process being of the type wherein an antigen or haptene is covalently linked to a tagging enzyme molecule to form a mixture of immunologically active and inactive conjugates, whereafter the mixture is subjected to separation processes the improvement comprising said separation process being based on chemical separation techniques and including the steps of placing a solution of said mixture of immunologically active and inactive conjugates in contact with an insoluble substance able to form a non-immunological insoluble complex reversibly with said active and said inactive conjugates, said reversible complex being most strongly formed with said active conjugates; separating the insoluble substance from said solution; and eluting the less strongly held active conjugates from the insoluble substance with a desorbent, thereby to separate the inactive conjugates from the active conjugates.

2. Process as claimed in claim 1 wherein said complex former is insolubilized by binding it to an insoluble carrier.

3. Process as claimed in claim 1 wherein the complex former is insolubilized by cross-linking same.

4. Process as claimed in claim 1 wherein said desorbent is selected from a dissolved complex former, an analog thereof and a detergent.

5. Process as claimed in claim 1 wherein the said antigen is a protein not having enzymatic properties and wherein said complex former is a binding component therefor consisting of steroids, fatty acids and hormones.

6. Process as claimed in claim 1 wherein said antigen is an enzymatically active protein and wherein said complex former is selected from the group consisting of co-enzymes, substrates, substrate analogs and inhibitors.

7. Process as claimed in claim 1 wherein said conjugate has a haptene component having hormonal character and said complex former is selected from the group consisting hormone-forming proteins and low molecular weight substances.

8. The process of claim 1 wherein said insoluble substance is bovine serum albumin-sepharose.

9. The process of claim 8 wherein said insoluble substance is thyroxine-sepharose.

10. Method of separating immunologically active enzyme tagged antigens or haptenes from a mixture thereof with immunologically inactive ones of the same enzyme tagged antigens or haptenes, comprising the steps of placing a solution of said mixture of immunologically active and inactive conjugates in contact with an insoluble substance able to form a non-immunological insoluble complex reversibly with said active and said inactive conjugates, said reversible complex being most strongly formed with said active conjugates; separating the insoluble substance from said solution; and eluting the less strongly held inactive conjugates and thereafter the more strongly held active conjugates from the insoluble substance with a desorbent, thereby to separate the inactive conjugates from the active conjugates.

* * * * *